US010138085B2

(12) United States Patent
Ehrhardt

(10) Patent No.: US 10,138,085 B2
(45) Date of Patent: Nov. 27, 2018

(54) CLEAR CARD SENSORS

(71) Applicant: ZIH CORP., Lincolnshire, IL (US)

(72) Inventor: Robert A. Ehrhardt, Palatine, IL (US)

(73) Assignee: ZIH Corp., Lincolnshire, IL (US)

( * ) Notice: Subject to any disclaimer, the term of this patent is extended or adjusted under 35 U.S.C. 154(b) by 0 days.

(21) Appl. No.: 14/670,961

(22) Filed: Mar. 27, 2015

(65) Prior Publication Data

US 2016/0280486 A1    Sep. 29, 2016

(51) Int. Cl.
*B65H 7/02* (2006.01)
*B65H 7/14* (2006.01)
(Continued)

(52) U.S. Cl.
CPC ............ *B65H 7/14* (2013.01); *B41J 11/0095* (2013.01); *B65H 7/04* (2013.01); *B65H 7/20* (2013.01); *G01N 2021/558* (2013.01)

(58) Field of Classification Search
CPC ... B65H 7/02; B65H 7/04; B65H 7/14; B65H 2511/51; B65H 2553/414; B65H 7/20; B41J 11/0095
(Continued)

(56) References Cited

U.S. PATENT DOCUMENTS

| 4,281,244 A * | 7/1981 | Murata | ................ | B41J 11/0095 |
| | | | | 250/223 R |
| 6,600,167 B2 * | 7/2003 | Sano | ........................ | G01V 8/20 |
| | | | | 250/559.11 |

(Continued)

FOREIGN PATENT DOCUMENTS

| EP | 0385417 A2 | 9/1990 |
| EP | 0623894 A1 | 11/1994 |

(Continued)

OTHER PUBLICATIONS

International Search Report and Written Opinion from corresponding International Patent Application No. PCT/US2016/017996 dated Jun. 1, 2016.

*Primary Examiner* — Thomas A Morrison

(57) ABSTRACT

Systems, methods, and apparatuses are disclosed for sensing clear or transparent media in printers. In one embodiment, a media conveyance apparatus is provided comprising a light sensor positioned on a first side of a media conveyance path; a light source positioned on a second side of the media conveyance path; and presence determination circuitry. The media conveyance apparatus is configured such that the light sensor and the light source are positioned such that media may pass between the light sensor and the light source along the media conveyance path. The media conveyance apparatus is further configured such that the light sensor provides signals to the presence determination circuitry indicating an amount of light received from the light source and the presence determination circuitry determines a reflection loss based on the signals received from the light sensor and further determines whether the reflection loss satisfies a loss threshold. The media conveyance apparatus is further configured so that if the presence determination circuitry determines the reflection loss satisfies the loss threshold, the presence determination circuitry outputs a media present indication.

15 Claims, 7 Drawing Sheets

(51) Int. Cl.
*B65H 7/04* (2006.01)
*B65H 7/20* (2006.01)
*B41J 11/00* (2006.01)
*G01N 21/55* (2014.01)

(58) Field of Classification Search
USPC .............. 250/559.4, 559.41, 559.42, 559.49,
250/559.46, 559.11, 559.01, 559.04,
250/559.12, 559.13, 559.16, 559.17;
271/258.01, 265.01
See application file for complete search history.

(56) References Cited

U.S. PATENT DOCUMENTS

| | | | |
|---|---|---|---|
| 7,433,614 B2* | 10/2008 | Suzuki | B65H 7/14 |
| | | | 399/389 |
| 2005/0078973 A1* | 4/2005 | Suzuki | B65H 7/14 |
| | | | 399/45 |
| 2006/0091331 A1 | 5/2006 | Tanamachi | |

FOREIGN PATENT DOCUMENTS

| | | |
|---|---|---|
| EP | 1510484 A1 | 3/2005 |
| WO | 2009136129 A1 | 11/2009 |

\* cited by examiner

CLEAR CARD SENSORS

FIELD

Embodiments discussed herein are related to printer sensors and, more particularly, to systems, methods, apparatuses, and other means for sensing clear or transparent media in printers.

BACKGROUND

A number of deficiencies and problems associated with sensing clear or transparent media in a printer are identified herein. Through applied effort, ingenuity, and innovation, exemplary solutions to many of these identified problems are embodied by the present invention, which is described in detail below.

BRIEF SUMMARY

Systems, methods, and apparatuses are disclosed for sensing clear or transparent media in printers. Embodiments of the present invention comprise one or more sensors that may be used in sensing clear or transparent printer media. For example, such clear/transparent printer media may comprise polyvinyl chloride (PVC) cards without infrared (IR) absorbing layers and/or PVC cards with IR absorbing layers. In some embodiments, printer media may comprise materials other than PVC cards, for example, materials such as polyethylene terephthalate (PET), polyethylene, or the like.

In one embodiment, a media conveyance apparatus is provided comprising a light sensor positioned on a first side of a media conveyance path; a light source positioned on a second side of the media conveyance path; and presence determination circuitry. The light sensor and the light source being positioned such that media passes between the light sensor and the light source along the media conveyance path. The apparatus is further configured such that the light sensor provides signals to the presence determination circuitry indicating an amount of light received from the light source and the presence determination circuitry determines a reflection loss based on the signals and further determines whether the reflection loss satisfies a loss threshold. The apparatus is further configured such that if the presence determination circuitry determines the reflection loss satisfies the loss threshold, the presence determination circuitry outputs a media present indication.

In some embodiments, the media conveyance apparatus may further comprise a second light sensor, wherein the second light sensor provides a reference to compensate for environmental changes, and wherein the second light sensor is positioned to detect an amount of light transmitted by the light source regardless of the presence or absence of the media along the media conveyance path.

In some embodiments, the media conveyance apparatus may be further configured wherein the light source is positioned such that a path from the light source to the media in the media conveyance path is between 30 degrees and 60 degrees from normal. In some embodiments, the media conveyance apparatus may be configured wherein the light source is positioned such that a path from the light source to the media in the media conveyance path may be 45 degrees from normal. While the example embodiments are described with paths from the light source to the media between 30° and 60° from normal, this range is not intended as a limit, but rather is only provided as an example. Paths from the light source to the media outside the range of 30° to 60° from normal may be provided for in some embodiments and are within the scope of the invention.

In some embodiments, the media may comprise transparent polyvinyl chloride media without infrared absorbing layers. In some embodiments, the media may comprise transparent polyvinyl chloride media with infrared absorbing layers. In some embodiments, the reduction in the amount of light received from the light source is due to first surface reflection loss caused by the media.

In some embodiments, the apparatus may be further configured wherein the reflection loss is within a defined range. In some embodiments, the reflection loss is between 10 percent and 20 percent. While the example embodiments provided are described with a detected reflection loss between 10 and 20 percent, this range is not intended as a limit, but rather is only provided as an example. Reflection loss percentages outside the range of 10 to 20 percent may be provided for in some embodiments and are within the scope of the invention.

In some embodiments, the light sensor and/or the second sensor may comprise phototransistors. In some embodiments, the light sensor and/or the second sensor may comprise photodiodes. In some embodiments, the light source is a light emitting diode. In some embodiments, the light source may be an incandescent lamp. In some embodiments, the media conveyance apparatus is comprised within a printer.

In another embodiment, a method is provided that includes receiving, from a light sensor, signals indicating an amount of light received from a light source and determining, by processing circuitry, a reflection loss based on the signals received from the light sensor. The method further includes determining whether the reflection loss satisfies a loss threshold. If the reflection loss satisfies a loss threshold, the method further includes outputting a media present indication.

In some embodiments, the method further comprises receiving measurements from a second light sensor for use in compensating for environmental effects in the determining of the reflection loss. In some embodiments, compensation may be made for other causes of component changes, such as component changes from ageing or variations in supply voltage, for example.

In some embodiments, the method further comprises wherein the light source is positioned such that a path from the light source to media in the media conveyance path is between 30° to 60° from normal. In some embodiments, the method further comprises wherein the light source is positioned such that a path from the light source to media in the media conveyance path is 45° from normal. While the example embodiments provided are described with paths from the light source to media in the media conveyance path between 30° and 60° from normal, this range is not intended as a limit, but rather is only provided as an example. Paths from the light source to media outside the range of 30° to 60° from normal may be provided for in some embodiments and are considered within the scope of the invention.

In some embodiments, the media may comprise transparent polyvinyl chloride media without infrared absorbing layers. In some embodiments, the media may comprise transparent polyvinyl chloride media with infrared absorbing layers.

In some embodiments, the method further comprises wherein the reduction in the amount of light received from the light source is due to first surface reflection loss caused by the media in the media conveyance path. In some embodiments, the method further comprises wherein the reflection loss is within a defined range. In some embodiments, the method further comprises wherein the reflection loss is between 10 percent and 20 percent. While the example embodiments provided are described with a detected reflection loss between 10 and 20 percent, this range is not intended as a limit, but rather is only provided as an example. Reflection loss percentages outside the range of 10 to 20 percent may be provided for in some embodiments and are within the scope of the invention.

In another embodiment, a media conveyance apparatus is provided comprising a light sensor positioned on a first side of a media conveyance path; a light source positioned on a second side of the media conveyance path; and presence determination circuitry. The light sensor and the light source being positioned such that media passes between the light sensor and the light source along the media conveyance path. The apparatus is further configured such that the light sensor provides signals to the presence determination circuitry indicating an amount of light received from the light source. The apparatus is further configured such that the presence determination circuitry determines the transmitted light received based on the signals and further determines whether the transmitted light received is within a first amount of light range. The apparatus is further configured such that if the presence determination circuitry determines the transmitted light received is within the first amount of light range, the presence determination circuitry outputs a media not present indication. The apparatus is further configured such that if the presence determination circuitry determines the transmitted light received is not within the first amount of light range, the presence determination circuitry determines whether the transmitted light received is within a second amount of light range. The apparatus is further configured such that if the presence determination circuitry determines the transmitted light received is within the second amount of light range, the presence determination circuitry outputs a media present indication.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 provides a simplified illustration of an exemplary clear card sensor in accordance with some embodiments of the present invention;

DETAILED DESCRIPTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Overview

Embodiments of the present invention are directed to methods, systems, and apparatuses for sensing clear or transparent media in printers. Embodiments of the present invention provide for one or more sensors that can be used to sense clear or transparent printer media. For example, such printer media may comprise polyvinyl chloride (PVC) cards without infrared (IR) absorbing layers and/or PVC cards with IR absorbing layers. In some embodiments, printer media may comprise materials other than PVC cards, for example, materials such as polyethylene terephthalate (PET), polyethylene, or the like. Embodiments of the present invention may be used to identify media that provide at least some level of reflection of transmitted light incident to the first surface of the media. In example embodiments, the sensor is configured to detect first surface reflection loss caused by one or more types of reflection of some portion of the transmitted light from the first surface of the media, such as one or more of specular reflection, diffuse reflection, or spread reflection.

Example Clear Card Sensor

Figure 1:
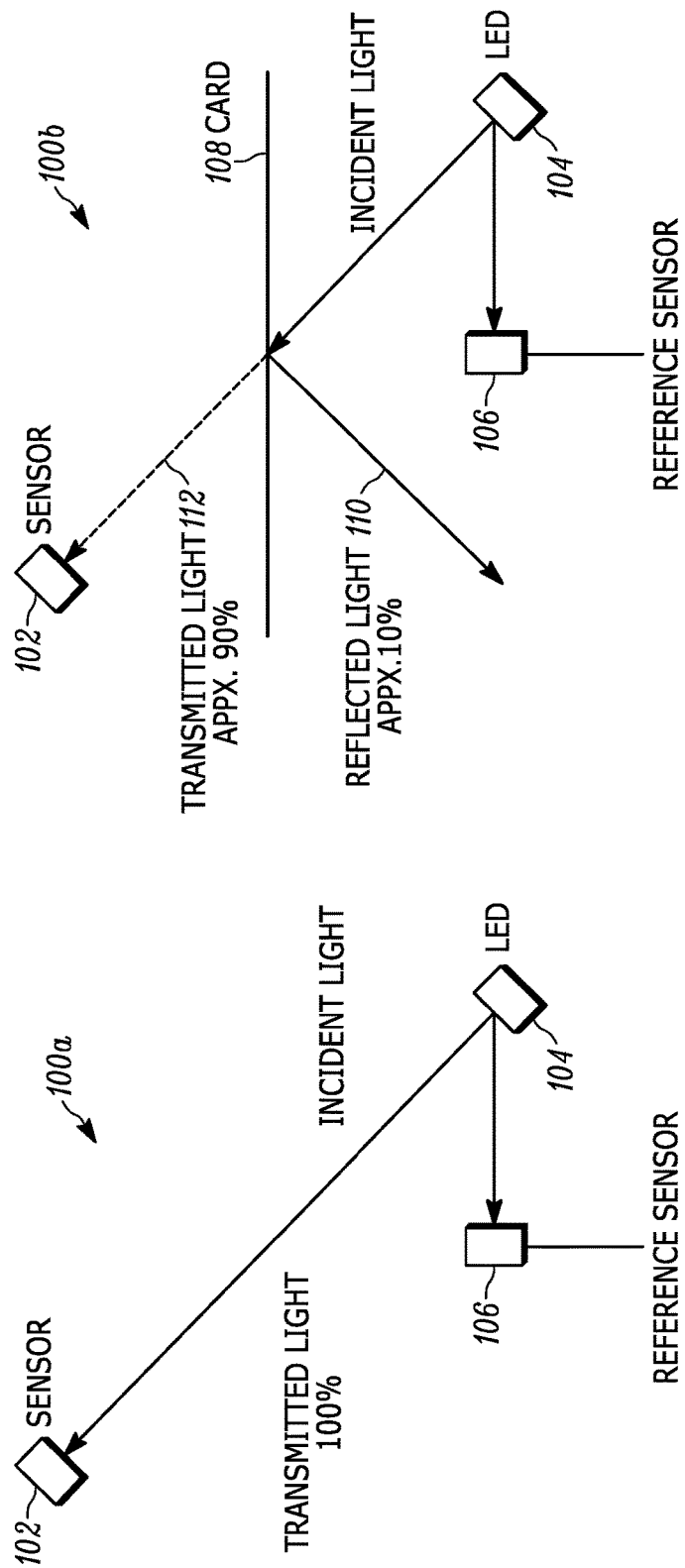

FIG. 1 provides a simplified illustration of an exemplary clear card sensor in accordance with some embodiments of the present invention. The clear card sensor utilizes first surface reflection loss of a light transmission to detect media. For example, embodiments may be used to detect clear or transparent media whose first surface provides at least some level of reflectance of incident light. In the example embodiment illustrated in FIG. 1, the clear card sensor comprises a sensor 102, an LED light source 104, and, optionally, a reference sensor 106.

As illustrated in clear card sensor 100a of FIG. 1, the sensor 102 is positioned such that it looks at the light transmitted by light source 104, and the sensor 102 and light source 104 are positioned such that media may pass between the sensor 102 and the light source 104 along a media conveyance path. FIG. 1 illustrates an example embodiment of a clear card sensor where the transmission light path from the LED light source 104 to the sensor 102 (e.g., a path or line formed between the transmission light source 104 output and the sensor 102 input) is 45° from the normal of media in the media conveyance path. In some embodiments, other transmission light paths may be chosen, such as transmission light paths between 30° and 60° from normal. While the example embodiments provided are described with transmission light paths between 30° and 60° from normal, this range is not intended as a limit, but rather this range is only provided as an example. Transmission light paths outside the range of 30° to 60° from normal may be provided for in some embodiments and are considered within the scope of the invention. For example, any transmission light path from 10° to 80° from the normal of the media conveyance path may be used in some embodiments.

As illustrated in clear card sensor 100a, when no media is present between the sensor and the light source, the sensor 102 sees the entire incident light, or nearly the entire incident light, transmitted along the path by light source 104. As illustrated in clear card sensor 100b, when media, such as card 108, is present between the sensor 102 and light source 104 along the media conveyance path, a portion of the incident light from light source 104 is reflected from a first surface of the media, such as reflected light 110, and only the portion of the light transmitted through the media, such as transmitted light 112, is seen by the sensor 102. In example embodiments, the type of reflection may comprise one or more of specular, diffuse, or spread reflection.

In example embodiments, the clear card sensor may comprise circuitry configured to receive signals from one or more sensors, e.g., sensor 102, generated by the sensor detecting some portion of transmitted light from the light source, e.g., light source 104. The clear card sensor circuitry may be further configured to determine that the signal received from the sensor indicates a reduction in the amount of transmitted light being received by the sensor (e.g., a reflection loss). The circuitry may then determine that the received signal indicates the presence of clear/transparent media between the sensor and the light source along the media conveyance path, such as by determining that the reduction in the amount of transmitted light being received by the sensor is within a defined range.

Figure 2:
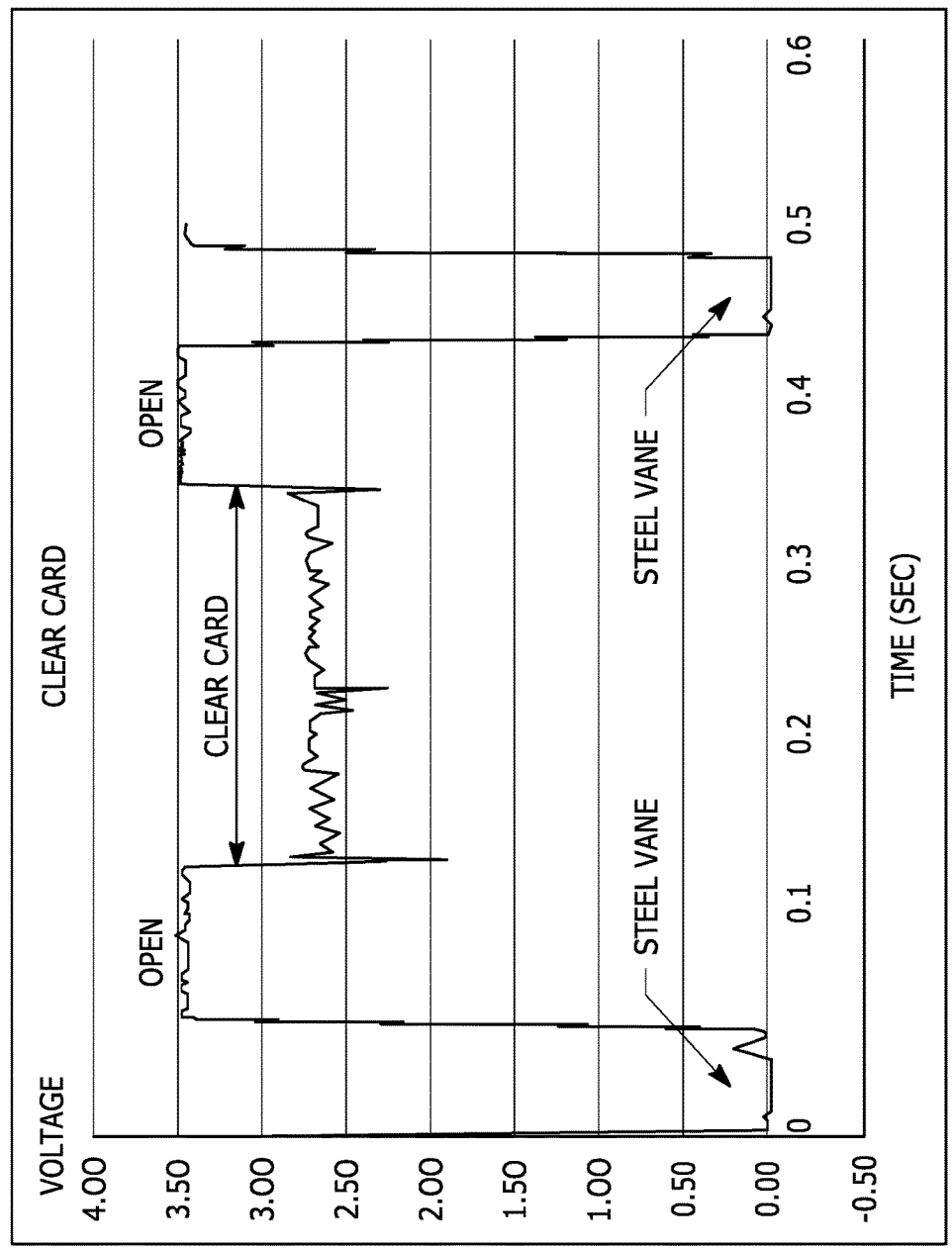
FIG. 2 illustrates an exemplary waveform illustrating the observed reflection loss by a clear card sensor in accordance with some embodiments of the present invention.

For example, as illustrated by the exemplary sensor waveform of FIG. 2, in one embodiment the observed reflection loss may be approximately twenty percent when the media, such as clear card 108, is present between sensor 102 and light source 104. While the illustrated sensor waveform is shown with a detected reflection loss of approximately twenty percent, this is not intended as a limit, but rather is only provided as an example. Reflection loss percentages in other ranges may be provided for in some embodiments and are considered within the scope of the invention.

Detecting this small loss due to reflection requires a stable sensor system where care is taken to compensate for environmental changes. In some embodiments, optional reference sensor 106 may be provided to compensate for environmental and/or component changes, such as changes in light, power supply voltage, ambient temperature, and/or the like.

In some embodiments, the clear card sensor may use a determination of an amount of transmitted light received instead of a reflection loss to determine whether media is present between the light sensor and the light source. For example, the clear card sensor may determine that the transmitted light received is within a first range (e.g., equal to or greater than 90%, between 90% and 100%) and indicate that media is not present. The clear card sensor may determine that the transmitted light received is within a second range (e.g., less than 90%, 0% up to 90%) and indicate that clear/transparent media is present between the light sensor and the light source along a conveyance path.

In some embodiments, the optional reference sensor 106 is a phototransistor arranged to be aligned with the light source 104, as illustrated in FIG. 1, where the presence or absence of media does not affect the transmission of light from the light source 104 to reference sensor 106. In some embodiments, the reference sensor need not be directly aligned with the light source, but instead be positioned to monitor changes in the detected output of the light source regardless of the presence or absence of any media. The reference sensor 106 may be used to compensate for LED output variations, transistor temperature drift, other environmental or component changes, and the like. In some embodiments, the stability provided by the compensation scheme may eliminate the need for periodic sensor recalibration.

Example Circuit Design

Figure 3:
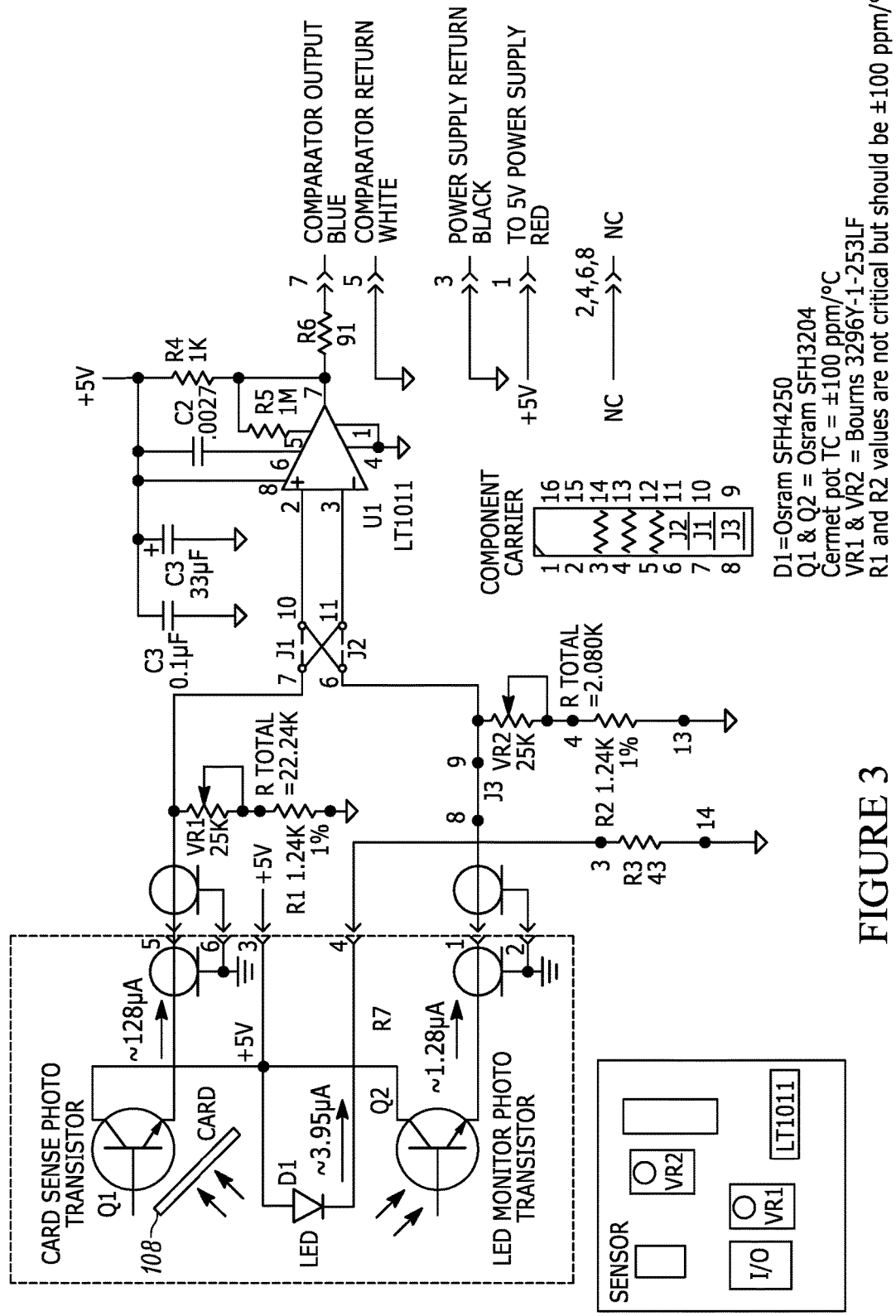
FIG. 3 illustrates a schematic of an exemplary clear card sensor in accordance with some embodiments of the present invention.

FIG. 3 illustrates a schematic of an exemplary clear card sensor in accordance with some embodiments of the present invention. The phototransistors (Q1) and (Q2) are connected in common-collector configuration with variable emitter resistors to set operating voltages. While phototransistors are described in the example embodiments, other sensor components, for example photodiodes or the like, may be used in some embodiments. The emitters are connected to the corresponding comparator inputs. The LED (D1) current is set by the fixed cathode resistor. While an LED light source is described in the example embodiments, other light sources, for example incandescent lamps or the like, may be used in some embodiments.

LED (D1) exposes the media sample and the current for LED (D1) is set by fixed cathode resistor (R3). Card sense phototransistor (Q1) is exposed to the LED light transmitted or reflected from the media, such as card 108. Variable emitter resistor (VR1) is used to set the operating voltages for the card sense phototransistor (Q1). LED monitor phototransistor (Q2) is provided for the reference sensor. This phototransistor looks directly at the LED (D1). Variable emitter resistor (VR2) is used to set the operating voltages for the LED monitor phototransistor (Q2).

In one example embodiment, the clear card sensor may be comprised of the following optical components.

LED: The Osram SFH 4250 was selected for its wide angle (±60°) and high output. The wide angle minimizes alignment sensitivity and the high output permits low current operation. Low current operation also minimizes heating of the reference phototransistor.

Phototransistors: Osram SFH 3204 devices were selected for their small size and wide viewing angle (±60°).

Comparator: The Linear Technology LT1011 was selected for its low offset voltage drift and high gain. This comparator has a guaranteed offset voltage drift of 15 $\mu V/°$ C. The drift specification is necessary to assure registration drift over temperature.

Trimpots: The temperature coefficient of the trimpot affects the registration drift over temperature. The trimpots affect each sensor independently so cancellation cannot be assumed. Bourns 3296Y series cermet devices were selected for their ±100 ppm/° C. temperature coefficients.

The temperature coefficient of each component of the clear card sensor may affect registration (sensing the presence of the media). The sensor can be decomposed into three subsystems: the card sensor, the reference sensor, and the LED system. Temperature drift of the LED system (LED and current limiting resistor) directly affects both the card subsystem (phototransistor and trimpot) and the reference subsystem (phototransistor and trimpot) equally. The resulting changes appear as a common mode input to the comparator and cancel out. Independent temperature drift of either card or reference subsystem appears as a differential error that does affect registration (sensing the presence of the media). In some embodiments, the card and reference phototransistors are mounted in close proximity and respond equally to ambient temperature changes, assuming the reference phototransistor is not heated by the LED.

In an example embodiment, the system components have the following temperature coefficients (tempcos):

LED flux tempco−0.5%/K; forward voltage tempco−0.7 mV/K

Phototransistor hFE tempco+0.3%/° C. to +0.6%/° C. at low to medium currents. At high current the tempco may become negative.

Trimpot tempco±100 ppm/° C.

Metal film fixed resistor tempco±100 ppm/° C.

Comparator offset voltage tempco+15 µV/° C.

The registration drift over temperature is calculated from the temperature deviation and component tempcos. The component contributions are combined to yield the variation in voltage at the comparator inputs. That voltage is multiplied by the sensor constant in inches/volt to yield the registration change in inches over temperature.

Reference Subsystem and Card Subsystem Tempco Polarity Issues

The cancellation of LED temperature effect relies on common mode cancellation between the card and reference sensors. Both sensors must have tempcos of the same polarity. If the sensors have opposite tempco polarity the temperature effects are intensified instead of being cancelled.

There are two mechanisms that can cause this problem: 1) excessively high phototransistor current and 2) tempco interaction between the phototransistor and LED.

Problem 1). The transistor's positive tempco range, stated above, is for low to medium currents. At high currents the tempco may become negative.

Problem 2). Negative tempco interaction. The flux tempco of the LED is typically −0.5%/° C. The h tempco of the phototransistors, at low to medium current, is between +0.3%/° C. and +0.6%/° C. The sum of LED and phototransistor tempcos can be negative or positive:

| LED | Phototransistor | Combined Tempco |
|---|---|---|
| −0.5%/° C. | +0.3%/° C. | −0.2%/° C. |
| −0.5%/° C. | +0.6%/° C. | +0.1%/° C. |

It is, therefore, possible to encounter combined tempcos of opposite polarity.

The following solutions are provided for such situations.

Solution 1). Keep the phototransistor current low, for instance less than 2 mA in an example embodiment, to avoid tempco inversions.

Solution 2). Add a component to provide a dominant tempco such that the result is always predictable. For example, adding a +0.5%/° C. tempco would cancel that of the LED. The resulting card and reference subsystem tempcos would then range from +0.3%/° C. to +0.6%/° C. Note that the LED flux tempco is specified as a typical value not the maximum. Therefore the added tempco should be greater than the typical value. In some embodiments, adding +1.0%/° C. may suffice. In one example, an analysis of four sensors yielded a maximum LED tempco of −0.9%/° C. and a minimum of −0.215%/° C.

The additional tempco must be applied to the LED to preserve common mode cancellation. An NTC thermistor added to the LED current setting resistor is one method. The negative resistance characteristic causes LED current to increase producing the desired positive tempco.

| LED | Phototransistor | Thermistor | Combined Tempco |
|---|---|---|---|
| −0.5%/° C. | +0.3%/° C. | +1.0%/° C. | +0.8%/° C. |
| −0.5%/° C. | +0.6%/° C. | +1.0%/° C. | +1.1%/° C. |

Figure 4:
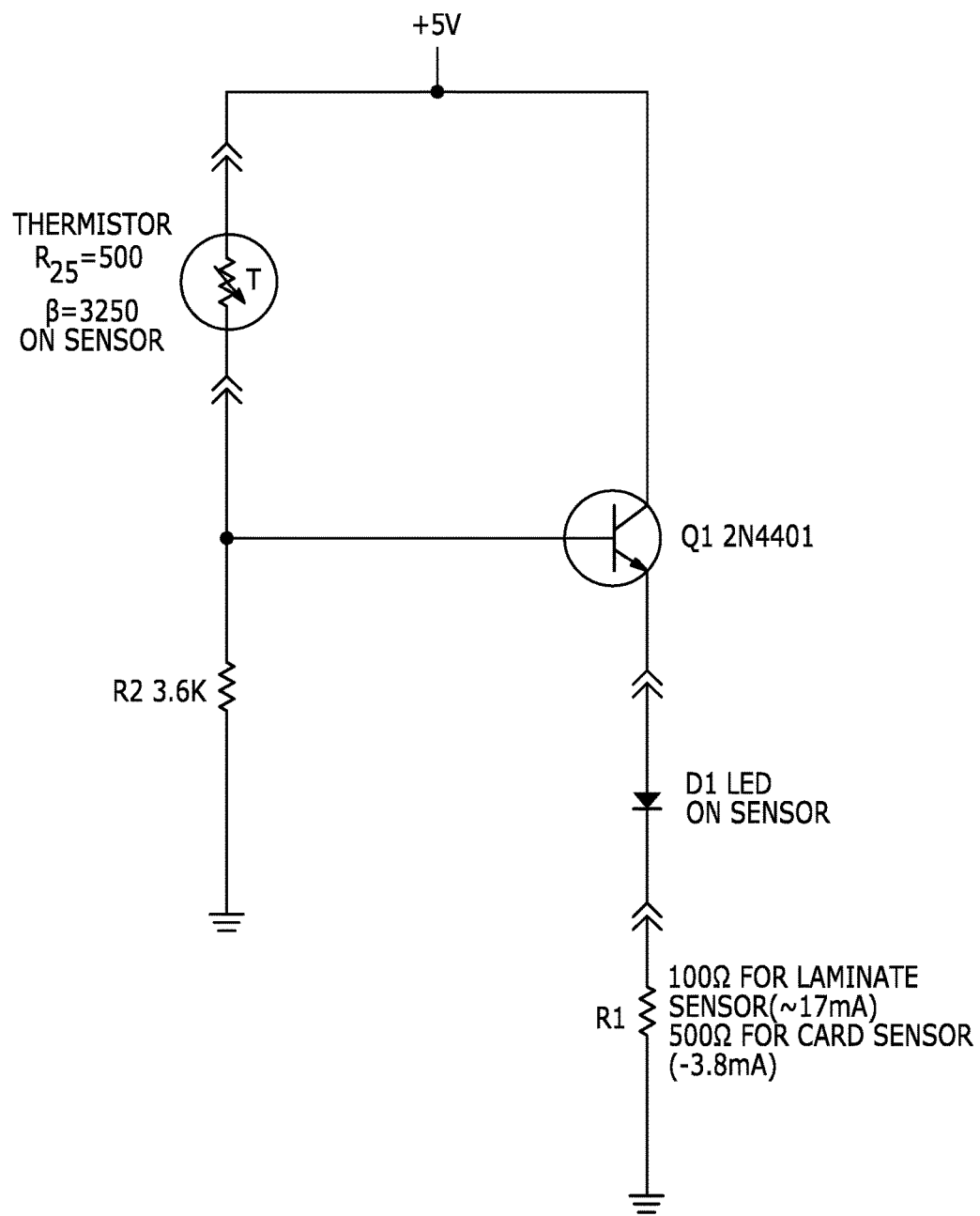
FIG. 4 illustrates a thermistor implementation in accordance with some embodiments of the present invention.

FIG. 4 illustrates one possible thermistor implementation. The thermistor operating current is limited to a couple of milliamps so a transistor buffer is required. Only the additional thermistor is mounted in the sensor assembly.

Noise and Registration

An important factor in achieving tight registration is control of noise. In an example embodiment, the card registration point moves 0.001" for every 16.8 mV of signal. That is a rather small amount considering all the noise sources within the printer: such as motors, logic circuits, printhead cables, and power supply noise. The condition is further aggravated by the relatively high impedance of the sensors (for example up to 30 KΩ).

Mechanical noise must be considered. For example, the card sensor housing should be designed to avoid twisting as temperature changes. For example, a shift in the relative locations of the sensor arms of 0.003" over 51° C. may violate the long-term specification. Vibrations of the mechanism between the sensor and printhead may easily exceed the 0.001" specification for short term registration.

Power Supply Sensitivity

In some embodiments, the card sensor position does change with power supply voltage. For example, in some embodiments, a change of 0.15V will produce a displacement of 0.001". Power supply stability should be carefully analyzed and if necessary augmented with a special post-regulator.

LED and Phototransistor Mounting

Reflections from printed circuit board (PCB) surfaces directly in front of these devices may produce unexpected problems. In some embodiments, a hole may be milled or punched in the PCB directly in front of the LED or phototransistor to reduce reflections. Alternatively, in some embodiments, reflections may be reduced by leaving the fiberglass surface bare and untreated.

Example Processes for Sensing Media

Figure 5:
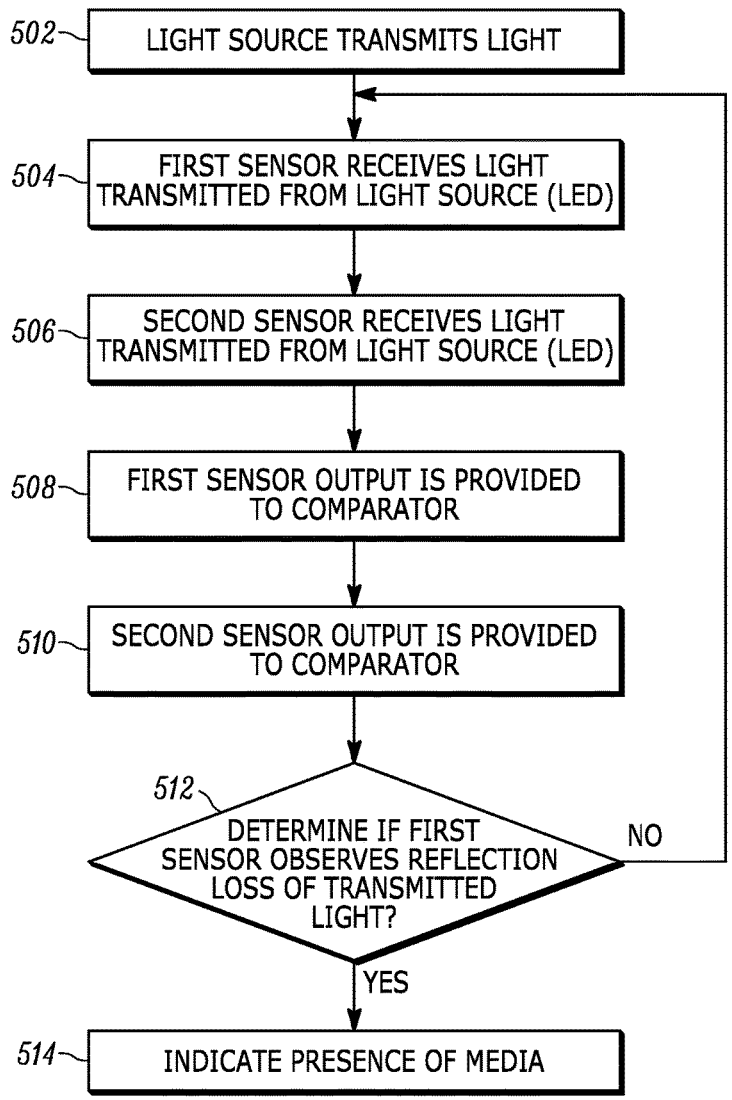
FIG. 5 illustrates a flowchart of an example process that may be used in sensing clear or transparent media in accordance with some embodiments of the present invention.

FIG. 5 illustrates a flowchart of an exemplary process for sensing clear or transparent media in accordance with some embodiments of the present invention. The process may start at block 502, where the light source, such as light source 104, transmits incident light. At block 504, the first sensor, such as sensor 102 (e.g., card sense phototransistor Q1), receives light transmitted by the light source. At block 506, the second sensor, such as sensor 106 (e.g., reference phototransistor Q1), also receives light transmitted by the light source.

At block 508, the output from the first sensor is provided as input, for example, to a comparator. At block 510, the output from the second sensor is provided as input, for example, to a comparator.

At block 512, a determination is made, for example using a comparator, whether the first sensor observes a reflection loss in the light transmitted by the light source. For example, clear or transparent media, such as card 108, may be present between the first sensor and the light source along a media conveyance path and cause a portion of the light transmitted to be reflected back from the first surface of the media.

If it is determined that no reflection loss is observed by the first sensor, operation loops back to block 502. Optionally an indication may be provided that media is not present between the light source and the first sensor. If it is determined that a reflection loss has been observed by the first sensor, an indication is provided that media is present between the light source and the first sensor at block 514.

Figure 6:
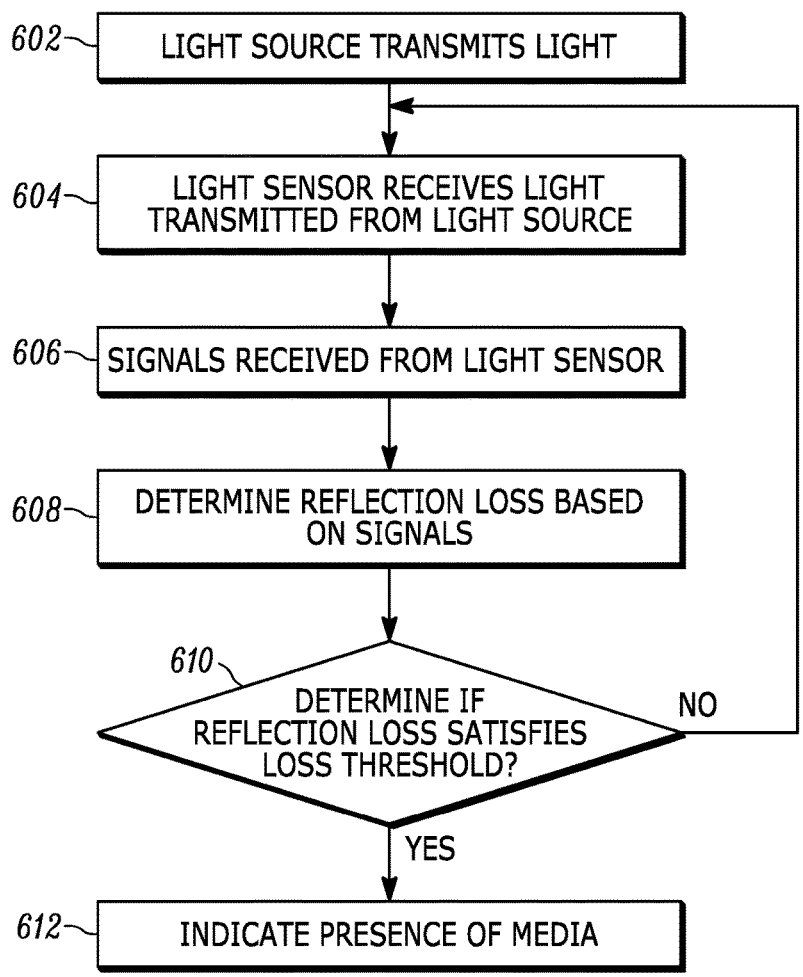
FIG. 6 illustrates a flowchart of an example process that may be used in sensing clear or transparent media in accordance with some embodiments of the present invention.

FIG. 6 illustrates a flowchart of an exemplary process for sensing clear or transparent media in accordance with some embodiments of the present invention. The process may start at block 602, where the light source, such as light source 104, transmits light toward the light sensor. At block 604, the light sensor, such as sensor 102, receives light transmitted by the light source.

At block 606, signals output from the light sensor are received, the signals indicating an amount of light received from the light source along a transmission light path. At block 608, a reflection loss is determined based on the signals from the light sensor. For example, clear or transparent media, such as card 108, may be present between the light sensor and the light source along a media conveyance path such that a reflection loss is caused by a portion of the light transmitted being reflected back from the first surface of the media (i.e., only a portion of the originally transmitted light passes through the media and is received at the light sensor).

At block 610, a determination is made whether the reflection loss satisfies a loss threshold. For example, a loss threshold may be defined wherein the reflection loss is between 10 percent and 20 percent.

If the reflection loss does not satisfy the loss threshold, operation may loop back to block 602. Optionally an indication may be provided that media is not present between the light source and the first sensor. If the reflection loss satisfies the loss threshold, an indication is provided that media is present between the light source and the first sensor at block 612.

Figure 7:
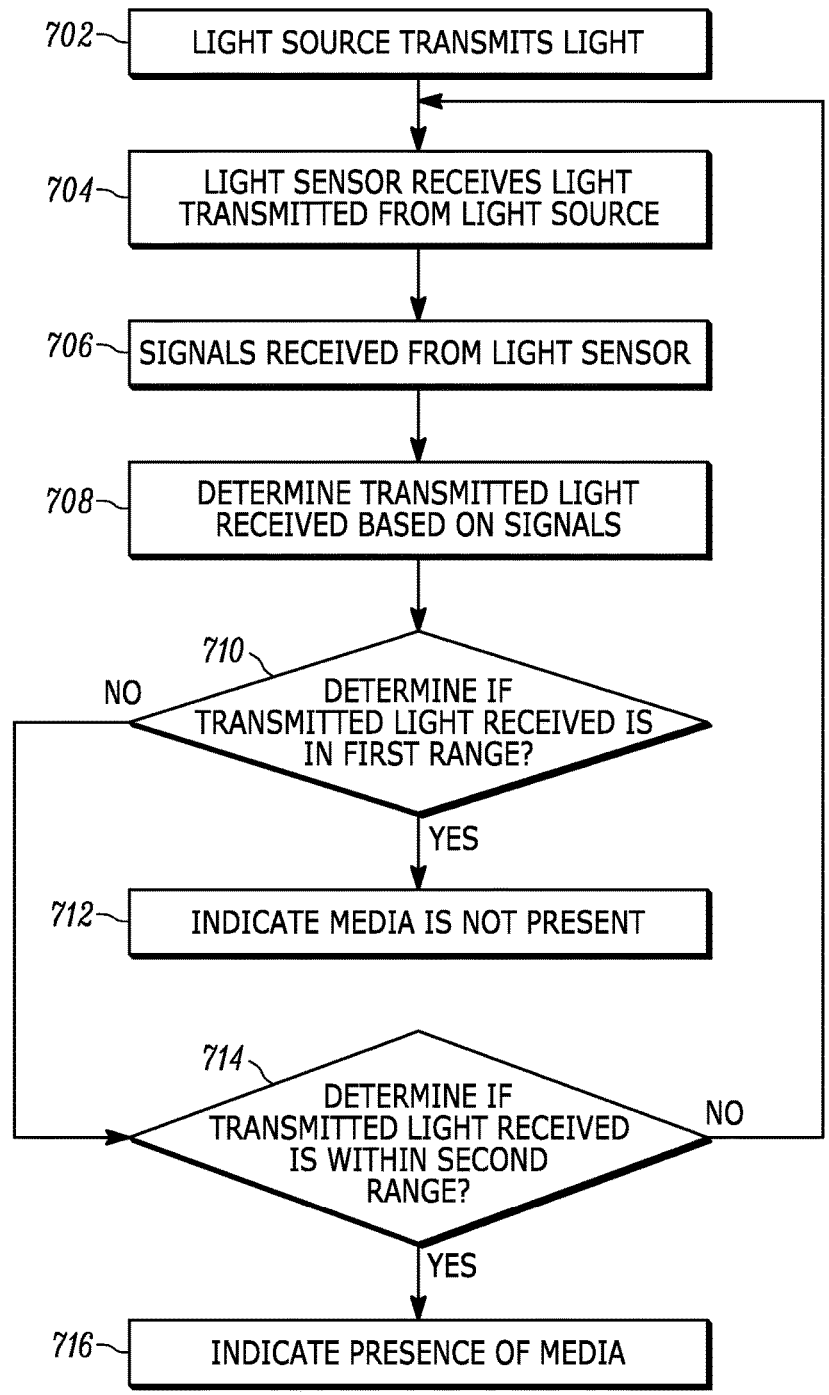
FIG. 7 illustrates a flowchart of an example process that may be used in sensing clear or transparent media in accordance with some embodiments of the present invention.

FIG. 7 illustrates a flowchart of another exemplary process for sensing clear or transparent media in accordance with some embodiments of the present invention. The process may start at block 702, where the light source, such as light source 104, transmits light toward the light sensor. At block 704, the light sensor, such as sensor 102, receives the light transmitted by the light source.

At block 706, signals output from the light sensor are received, the signals indicating an amount of light received from the light source along a transmission light path. At block 708, a determination is made of the transmitted light received based on the signals from the light sensor. For example, clear or transparent media, such as card 108, may be present between the light sensor and the light source along a media conveyance path such that only a portion of the light transmitted is received at the light sensor.

At block 710, a determination is made whether the amount of transmitted light received falls within a first range, for example, the light received at the light sensor is approximately 100% of the light transmitted, the light received is equal to or greater than 90%, etc. If the transmitted light received falls within the first range, an indication may be provided that media is not present between the light source and the first sensor at block 712.

If the transmitted light received is not within the first range, a determination is made whether the amount of transmitted light received falls within a second range (e.g., less than 90%, 0% up to 90%, etc.) at block 714.

If the transmitted light received is not within the second range, operation may loop back to block 702. If the transmitted light received is within the second range, an indication is provided that media is present between the light source and the first sensor at block 716.

In some embodiments, certain ones of the operations above may be modified or further amplified. Moreover, in some embodiments additional optional operations may also be included. It should be appreciated that each of the modifications, optional additions, or amplifications may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A media conveyance apparatus comprising:
   a first light sensor positioned on a first side of a media conveyance path, the first light sensor to generate a first signal indicative of a first amount of light received by the first light sensor;
   a light source positioned on a second side of the media conveyance path;
   a second light sensor positioned on the second side of the media conveyance path, wherein the second light sensor is to compensate for an environmental change by detecting a second amount of light transmitted by the light source regardless of the presence or absence of media along the media conveyance path, the first light sensor and the light source being positioned such that the media passes between the first light sensor and the light source along the media conveyance path; and
   presence determination circuitry configured to:
      compare the first signal to a second signal received from the second sensor;
      detect a reflection loss based on the comparison of the first and second signals; and
      if the reflection loss is detected based on the comparison of the first and second signals, generate a media present indication.

2. The media conveyance apparatus of claim 1 wherein the light source is positioned such that a path from the light source to the media in the media conveyance path is between 30 degrees and 60 degrees from normal.

3. The media conveyance apparatus of claim 1 wherein the light source is positioned such that a path from the light source to the media in the media conveyance path is 45degrees from normal.

4. The media conveyance apparatus of claim 1 wherein the media comprises transparent polyvinyl chloride media without infrared absorbing layers.

5. The media conveyance apparatus of claim 1 wherein the media comprises transparent polyvinyl chloride media with infrared absorbing layers.

6. The media conveyance apparatus of claim 1 wherein the reflection loss is due to first surface reflection loss caused by the media.

7. The media conveyance apparatus of claim 1 wherein the determined reflection loss is between 10 percent and 20 percent.

8. The media conveyance apparatus of claim 1 wherein the first light sensor comprises a phototransistor or photodiode.

9. The media conveyance apparatus of claim 1 wherein the first light sensor and the second light sensor comprise phototransistors or photodiodes.

10. The media conveyance apparatus of claim 1 wherein the light source is one of a light emitting diode or an incandescent lamp.

11. The media conveyance apparatus of claim 1 wherein the media conveyance apparatus is comprised within a printer.

12. The media conveyance apparatus of claim 1, wherein the environmental change includes a change in power supply voltage.

13. A media conveyance apparatus comprising:
a first light sensor positioned on a first side of a media conveyance path;
a light source positioned on a second side of the media conveyance path, the light source to transmit light;
a reference sensor positioned on the second side of the media conveyance path, wherein the reference sensor is to compensate for environmental changes by detecting a reference amount of light transmitted by the light source regardless of presence or absence of media along the media conveyance path; and
presence determination circuitry;
the first light sensor and the light source being positioned such that the media passes between the first light sensor and the light source along the media conveyance path;
the first light sensor to provide a first signal to the presence determination circuitry indicating a first amount of light received from the light source at a first time;
the reference sensor to provide a reference signal to the presence determination circuitry indicating the reference amount of light at the first time;
the presence determination circuitry is configured to:
  determine, based on a comparison of the first signal and the reference signal, whether a reflection loss in the transmitted light is present;
  if the presence determination circuitry does not detect the reflection loss in the transmitted light, generate a media not present indication; and
  if the presence determination circuitry detects the reflection loss in the transmitted light, generate a media present indication.

14. The media conveyance apparatus of claim 13 wherein the media conveyance apparatus is comprised within a printer.

15. The media conveyance apparatus of claim 13, wherein the environmental change includes a change in power supply voltage.

* * * * *